United States Patent [19]

Klenk

[11] Patent Number: 4,492,793
[45] Date of Patent: Jan. 8, 1985

[54] PROCESS FOR THE PRODUCTION OF 2-AMINO-5-MERCAPTO-1,3,4-THIADIAZOLE

[75] Inventor: Herbert Klenk, Hanau, Fed. Rep. of Germany

[73] Assignee: Degussa Aktiengesellschaft, Frankfurt, Fed. Rep. of Germany

[21] Appl. No.: 408,131

[22] Filed: Aug. 13, 1982

[30] Foreign Application Priority Data

Aug. 21, 1981 [DE] Fed. Rep. of Germany ....... 3133096

[51] Int. Cl.$^3$ ............................................ C07D 285/12
[52] U.S. Cl. .................................................. 548/141
[58] Field of Search ........................................ 548/141

[56] References Cited

PUBLICATIONS

Guha, J. Am. Chem. Soc., vol. 44, pp. 1510–1517, (1922).
Chem. Abst. vol. 78, No. 111217f, (1973).
Katritzky et al, Advances in Heterocyclic Chemistry, vol. 9, p. 190, (1968).

Primary Examiner—Robert Gerstl
Attorney, Agent, or Firm—Cushman, Darby & Cushman

[57] ABSTRACT

2-Amino-5-mercapto-1,3,4-thiadiazoles can be produced in very high yields from thiosemicarbazides and carbon disulfide in aqueous phase by working in the presence of the corresponding ammonium salt of bis-2,5-mercapto-1,3,4-thiadiazole at a temperature above 40° C. Preferably the process is carried out in the presence of the mother liquor from a previous reaction.

21 Claims, No Drawings

PROCESS FOR THE PRODUCTION OF 2-AMINO-5-MERCAPTO-1,3,4-THIADIAZOLE

The invention is directed to a process for the production of 2-amino-5-mercapto-1,3,4-thiadiazoles of the general formula (I)

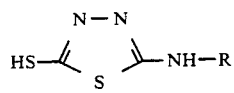   (I)

by reaction of a thiosemicarbazide of the general formula (II)

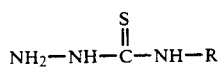   (II)

with carbon disulfide. Such thiadiazoles are valuable intermediate products for the synthesis of corrosion inhibitors, pharmaceuticals, photography chemicals and for pesticides.

It is known to produce such 1,3,4-thiadiazoles by reaction of thiosemicarbazides with xanthates. The production of xanthates from alcohols and carbon disulfide, however, is cumbersome and means an additional process step. Besides the yields obtainable are small. Thus, for example, in the production of 2-mercapto-5-methylamino-1,3,4-thiadiazole from 4-methyl-thiosemicarbazide and ethyl xanthate, there is only obtained a yield of 47% (Rothgery U.S. Pat. No. 4,252,962).

A further process is known which starts from hydrazine and thiocyanates. This process, however, is only usable for the production of the unsubstituted compounds. A further disadvantage is that the thiocyanates in part are very expensive material. (Song U.S. Pat. No. 2,966,495).

It is known furthermore to start from thiosemicarbazides and carbon disulfide in the production of these thiadiazoles. This is a very good process, but suffers from the fact that it can only be carried out in organic solvents. As especially advantageous solvent there is used an acid amide such as dimethyl formamide. However, precisely solutions of toxic materials, such as thiosemicarbazides, in dimethyl formamide are very dangerous since these solutions have a high ability to penetrate through the skin of humans. Furthermore, the desired thiadiazoles generally are obtained by precipitation with water from the organic solvents. However, through this there results an aqueous-organic mother liquor from which the expensive organic solvent can be recovered only with great effort (French Pat. No. 1,064,234 and Great Britain Pat. No. 726,045).

A reaction in aqueous solution according to the state of the art is not feasible since the desired reaction in general does not occur or forms too many byproducts.

SUMMARY OF THE INVENTION

It has now been found that 1,3,4-thiadiazoles of the general formula (I)

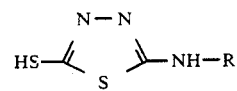   (I)

wherein R is a straight or branched chain alkyl group having 1 to 10 carbon atoms, which in a given case can also be substituted, a cycloalkyl group having 3 to 6 carbon atoms, a phenyl group which in a given case is substituted or especially a hydrogen atom or preferably a methyl group can be produced in high yields by reaction of a thiosemicarbazide of the general formula (II)

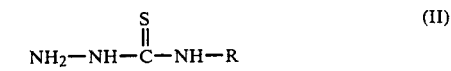   (II)

where R is as defined above, with carbon disulfide in aqueous phase, if the aqueous phase contains 15 to 70 weight % of an ammonium salt of the bis-2,5-mercapto-1,3,4-thiadiazole of the general formula (III)

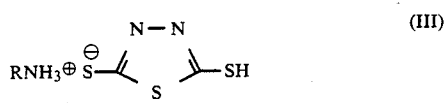   (III)

in which R is as defined above, and the reaction is carried out at a temperature above 40° C.

Examples of compounds within formula (I) include:
2-amino-5-mercapto-1,3,4-thiadiazole,
5-methylamino-2-mercapto-1,3,4-thiadiazole,
2-ethylamino-5-mercapto-1,3,4-thiadiazole,
5-propylamino-2-mercapto-1,3,4-thiadiazole,
2-isopropylamino-5-mercapto-1,3,4-thiadiazole,
2-n-butylamino-5-mercapto-1,3,4-thiadiazole,
2-isobutylamino-5-mercapto-1,3,4-thiadiazole,
2-sec.butylamino-5-mercapto-1,3,4-thiadiazole,
2-t-butylamino-5-mercapto-1,3,4-thiadiazole,
2-amylamino-5-mercapto-1,3,4-thiadiazole,
2-hexylamino-5-mercapto-1,3,4-thiadiazole,
5-octylamino-2-mercapto-1,3,4-thiadiazole,
2-decylamino-5-mercapto-1,3,4-thiadiazole,
2-cyclopropylamino-5-mercapto-1,3,4-thiadiazole,
2-cyclopentylamino-5-mercapto-1,3,4-thiadiazole,
2-cyclohexylamino-5-mercapto-1,3,4-thiaziazole, and
5-phenylamino-2-mercapto-1,3,4-thiadiazole.

Examples of compounds within formula (II) include:
thiosemicarbazide,
4-methylthiosemicarbazide,
4-ethylthiosemicarbazide,
4-propylthiosemicarbazide,
4-isopropylthiosemicarbazide,
4-n-butylthiosemicarbazide,
4-isobutylthiosemicarbazide,
4-sec.butylthiosemicarbazide,
4-t-butylthiosemicarbazide,
4-amylthiosemicarbazide,
4-hexylthiosemicarbazide,
4-octylthiosemicarbazide,
4-decylthiosemicarbazide,
4-cyclcopropylthiosemicarbazide,
4-cyclopentylthiosemicarbazide,
4-cyclohexylthiosemicarbazide and
4-phenylthiosemicarbazide Examples of compounds within formula (III) include the:

ammonium salt of 2,5-dimercaptothiadiazole,
methylammonium salt of 2,5-dimercaptothiadiazole,
ethylammonium salt of 2,5-dimercaptothiadiazole,
propylammonium salt of 2,5-dimercaptothiadiazole,
isopropylammonium salt of 2,5-dimercaptothiadiazole,
n-butylammonium salt of 2,5-dimercaptothiadiazole,
isobutylammonium salt of 2,5-dimercaptothiadiazole,
sec.butylammonium salt of 2,5-dimercaptothiadiazole,
t-butylammonium salt of 2,5-dimercaptothiadiazole,
amylammonium salt of 2,5-dimercaptothiadiazole,
hexylammonium salt of 2,5-dimercaptothiadiazole,
octylammonium salt of 2,5-dimercaptothiadiazole,
decylammonium salt of 2,5-dimercaptothiadiazole,
cyclopropylammonium salt of 2,5-dimercaptothiadiazole,
cyclopentylammonium salt of 2,5-dimercaptothiadiazole,
cyclohexylammonium salt of 2,5-dimercaptothiadiazole and
phenylammonium salt of 2,5-dimercapththiadiazole.

The thiosemicarbazides used as starting compounds are known compounds and are generally obtained by reaction of the correspondingly substituted isothiocyanate with hydrazine. The reaction is not limited to specific thiosemicarbazides but can be used universally.

The reaction temperature can be varied within wide limits. However, generally temperatures above 40° C. are necessary since the reaction occurs rapidly only above this temperature. Preferably, there are used temperatures above 50° C. There can especially be employed temperatures between about 55° and about 100° C. Working above 100° C. is likewise possible but brings about no advantage.

Although, the pressure can be chosen substantially as desired, it is advantageous to carry out the reaction at normal pressure or at slight excess pressure. Preferred are pressures between 1 and 4 bar.

The compounds of general formula (III) need not be added separately. Since they form in the mother liquor in the reaction of the thiosemicarbazide (II) with carbon disulfide, according to a preferred variant of the process it is possible to simply proceed by using the mother liquors from previous charges. It is especially advantageous to use these mother liquors multiple times, they thus are recycled. Through this the reaction time is reduced very sharply and the yields of the thiadiazole increased considerably and frequently are almost quantitative. Surprisingly, this does not reduce the purity of the thiadiazole obtained. Thus, for example, over 200 cycles can be carried out with such a mother liquor without observing a change in the results.

Through such high degrees of recycling the amount of products removed for the most part is very small, which is valued as a particular advantage considering the toxicity and danger to the environment of most of the sulfur-nitrogen-compounds used.

The process is particularly easy to carry out on an industrial scale.

Unless otherwise indicated, all parts and percentages are by weight.

The process can comprise, consist essentially of or consist of the steps set forth with the stated materials.

The following examples illustrate the invention without limiting the extent of the thiadiazoles synthesized.

DETAILED DESCRIPTION

Comparison Example 1

There were present in an apparatus equipped with stirrer, reflux condenser and an escape for gas 600 ml of water and 105 grams of 4-methylthiosemicarbazide. There were then dropped in from a dropping container at 35° C. to 40° C. during 30 minutes 76 grams of carbon disulfide and then the reaction mixture heated at vigorous reflux for 24 hours. During this time, there is only ascertained a very slight development of gas. The charge was allowed to cool off and the solid material present filtered off with suction. A thin layer chromotographic investigation shows that this solid material consisted of only 5 to 10% of the desired thiadiazole, while the main amount is unreacted methylthiosemicarbazide.

Example 1

There was selected the same apparatus and the same material was present in the apparatus except that in place of 600 ml of water there were present 600 ml of a mother liquor in which the reaction had been carried out already five times. Already, shortly after the heating to reflux, there was observed a vigorous development of gas which after about 6 hours subsided. Therefore, the reaction was broken off at this time and after cooling the solid material filtered off with suction. After drying the solid material there were obtained 123 grams of 2-mercapto-5-methylamino-1,3,4-thiadiazole, which corresponds to a yield of 85%, having a melting point of 185° to 186° C.

Example 2

In an apparatus provided with stirrer, reflux condenser with attached line for leading off gas and a butterfly valve for regulating pressure, there were present 300 ml of an aqueous mother liquor with which there already had been carried out 20 of this type of reaction, as well as 45.5 grams of thiosemicarbazide. The mixture was then heated to 75° C. and then there was begun with the aid of a pump the dosing in of carbon disulfide. Already, shortly after the first addition of carbon disulfide there begins to form a certain internal pressure through the splitting off of hydrogen sulfide and the butterfly valve is then so regulated that an overpressure of 1 bar is established. In this manner, they were fed in 45 grams of carbon disulfide during 4 hours. Subsequently, the mixture was heated for 1 more hour at 90° C., and then the solution allowed to cool. Then the precipitated 2-amino-5-mercapto-1,3,4-thiadiazole was filtered off with suction, washed with a little water and dried. There were thus obtained 60 grams of solid product which corresponded to a yield of 90%. The thiadiazole had a melting point of 242° to 244° C.

Example 3

The procedure was as described in Example 2, but instead of thiosemicarbazide there were present 83.5 grams of 4-phenylthiosemicarbazide 83.5 grams of 4-phenylthiosemicarbazide. After the cooling and filtering with suction there were isolated 83.6 grams (=80% yield) of 2-phenylamino-5-mercapto-1,3,4-thiadiazole having a melting point of 208° to 210° C.

Example 4

There were present in the same apparatus as in Example 1, a solution of 400 grams of the methylammonium salt of 2.5-dimercaptothiadiazole in 400 ml of water and otherwise the procedure was as in Example 1. After drying of the isolated solid material there were obtained 124.5 grams, which corresponded to a yield of 86%, having a melting point of 186° C.

What is claimed is:

1. A process for the production of a 2-amino-5-mercapto-1,3,4-thiadiazoles of the formula I:

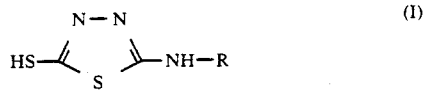
(I)

where R is hydrogen, an alkyl group of 1 to 10 carbon atoms, a cycloalkyl group of 5 to 6 carbon atoms or a phenyl group comprising reacting a thiosemicarbazide of the formula (II):

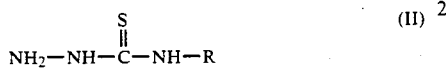
(II)

with carbon disulfide in aqueous phase wherein the aqueous phase has 15 to 70 weight % of an ammonium salt of bis-2,5-mercapto-1,3,4-thiadiazole of the formula (III):

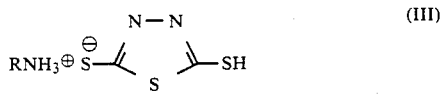
(III)

at a temperature above 40° and 100° C.

2. A process according to claim 1 where R is hydrogen.

3. A process according to claim 1, where R is alkyl of 1 to 10 carbon atoms.

4. A process according to claim 3, where R is methyl.

5. A process according to claim 1, where R is phenyl.

6. A process according to claim 1, wherein the aqueous phase comprises the mother liquor of at least one previous reaction.

7. A process according to claim 6, wherein the aqueous phase comprises the mother liquor from a plurality of previous reactions.

8. A process according to claim 7, wherein the aqueous phase comprises the mother liquor from at least 5 previous reactions.

9. A process according to claim 7, wherein the reaction is carried out at a temperature between 50° C. and 100° C. at normal or excess pressure.

10. A process according to claim 9, wherein the pressure is 1 to 4 bar.

11. A process according to claim 3, wherein the pressure is 1 to 4 bar.

12. A process according to claim 11, wherein the temperature is 55° to 100° C.

13. A process according to claim 1 wherein the temperature is 40° to 100° C.

14. A process according to claim 6 wherein the aqueous phase comprises the mother liquor from 1 to 200 previous reactions.

15. A process for the production of a 2-amino-5-mercapto-1,3,4-thiadiazoles of the formula I:

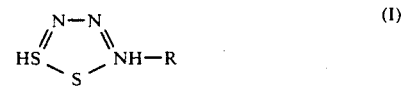
(I)

where R is hydrogen, an alkyl group of 1 to 10 carbon atoms, a cycloalkyl group of 5 to 6 carbon atoms or a phenyl group consisting essentially of reacting a thiosemicarbazide of the formula (II):

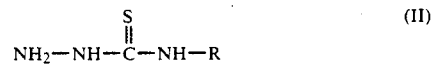
(II)

with carbon disulfide in aqueous phase wherein the aqueous phase has 15 to 70 weight % of an ammonium salt of bis-2,5-mercapto-1,3,4-thiadiazole of the formula (III):

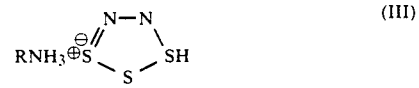
(III)

at a temperature about 40° and 100° C.

16. A process according to claim 15 where R is hydrogen.

17. A process according to claim 15 where R is alkyl of 1 to 10 carbon atoms.

18. A process according to claim 17 where R is methyl.

19. A process according to claim 1 where R is phenyl.

20. A process according to claim 15 wherein the aqueous phase comprises the mother liquor of at least one previous reaction.

21. A process according to claim 20 wherein the aqueous phase comprises the mother liquor from 1 to 200 previous reactions.

* * * * *